(12) United States Patent
Charles et al.

(10) Patent No.: US 10,806,918 B2
(45) Date of Patent: Oct. 20, 2020

(54) SYRINGE WITH DISINFECTING TIP FEATURE

(71) Applicant: Becton, Dickinson and Company, Franklin Lakes, NJ (US)

(72) Inventors: Nichola Charles, Budd Lake, NJ (US); Adam Zerda, Oak Ridge, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/270,878

(22) Filed: May 6, 2014

(65) Prior Publication Data

US 2014/0276449 A1 Sep. 18, 2014

Related U.S. Application Data

(63) Continuation of application No. 13/250,097, filed on Sep. 30, 2011, now Pat. No. 8,784,388.

(51) Int. Cl.
*A61M 39/16* (2006.01)
*A61M 39/14* (2006.01)
*A61M 39/00* (2006.01)

(52) U.S. Cl.
CPC .......... *A61M 39/162* (2013.01); *A61M 39/14* (2013.01); *A61M 2039/0018* (2013.01); *A61M 2205/19* (2013.01); *Y10T 29/49885* (2015.01)

(58) Field of Classification Search
CPC .... A61M 5/001; A61M 39/16; A61M 39/162; A61M 2205/0205; A61M 2209/10; A61M 39/10; A61M 2039/0018; A61M 2039/1077
See application file for complete search history.

(56) References Cited

U.S. PATENT DOCUMENTS

| | | | |
|---|---|---|---|
| 1,798,188 | A | 3/1931 | Brown |
| 2,677,373 | A | 5/1954 | Barradas |
| 2,961,682 | A | 11/1960 | Wurmbock et al. |
| 3,559,645 | A | 2/1971 | Schaller |
| 3,890,971 | A | 6/1975 | Leeson et al. |
| 3,976,311 | A * | 8/1976 | Spendlove .......... A61M 39/162 285/12 |
| 4,240,427 | A | 12/1980 | Akhavi |
| 4,243,035 | A | 1/1981 | Barrett |
| 4,273,123 | A | 6/1981 | Lemelson |
| 4,280,632 | A | 7/1981 | Yuhara |

(Continued)

FOREIGN PATENT DOCUMENTS

| | | |
|---|---|---|
| CN | 201046284 | 4/2008 |
| CN | 101405042 A | 4/2009 |

(Continued)

OTHER PUBLICATIONS

PCT International Preliminary Report on Patentability in PCT/US2012/054787, dated Apr. 1, 2014, 8 pages.

(Continued)

*Primary Examiner* — Kami A Bosworth
(74) *Attorney, Agent, or Firm* — Servilla Whitney LLC

(57) ABSTRACT

Syringe assemblies comprising a disinfecting reservoir collar to ensure an adherence to aseptic techniques for use in flush procedures for vascular access devices (VAD's) are described. Also described are methods of disinfecting the vascular access devices.

14 Claims, 11 Drawing Sheets

(56) References Cited

U.S. PATENT DOCUMENTS

| | | |
|---|---|---|
| 4,282,891 A | 8/1981 | Duceppe |
| 4,343,306 A * | 8/1982 | Mericle ............... A61M 5/001 |
| | | 604/218 |
| 4,354,490 A | 10/1982 | Rogers |
| 4,432,764 A | 2/1984 | Lopez et al. |
| 4,440,207 A | 4/1984 | Genatempo et al. |
| 4,444,310 A | 4/1984 | Odell |
| 4,624,664 A | 11/1986 | Peluso et al. |
| 4,626,664 A | 12/1986 | Grise |
| 4,655,762 A | 4/1987 | Rogers |
| 4,671,306 A | 6/1987 | Spector |
| 4,728,321 A | 3/1988 | Chen |
| 4,778,447 A | 10/1988 | Velde et al. |
| 4,799,926 A | 1/1989 | Haber |
| 4,874,384 A | 10/1989 | Nunez |
| 4,883,470 A | 11/1989 | Haindl |
| 4,991,629 A | 2/1991 | Ernesto et al. |
| 5,000,742 A | 3/1991 | Morrison |
| 5,026,345 A | 6/1991 | Teringo |
| 5,125,415 A | 6/1992 | Bell |
| 5,190,534 A * | 3/1993 | Kendell ............... B08B 3/048 |
| | | 604/6.16 |
| 5,195,957 A | 3/1993 | Tollini |
| 5,242,421 A | 9/1993 | Chan |
| 5,242,425 A | 9/1993 | White et al. |
| 5,334,388 A | 8/1994 | Hoang et al. |
| 5,336,192 A * | 8/1994 | Palestrant ......... A61M 39/0613 |
| | | 128/912 |
| 5,342,320 A | 8/1994 | Cameron |
| 5,527,283 A | 6/1996 | Swisher, III |
| 5,536,258 A * | 7/1996 | Folden ............... A61M 39/16 |
| | | 604/265 |
| 5,547,662 A | 8/1996 | Khan et al. |
| 5,554,135 A | 9/1996 | Menyhay |
| 5,639,310 A | 6/1997 | Giampaolo, Jr. |
| 5,694,978 A | 12/1997 | Heilmann et al. |
| 5,706,944 A | 1/1998 | Hoang et al. |
| 5,792,120 A | 8/1998 | Menyhay |
| 5,807,352 A | 9/1998 | Tamaro |
| 5,817,344 A | 10/1998 | Hoang et al. |
| 5,894,015 A | 4/1999 | Rechtin |
| 5,954,957 A | 9/1999 | Chin-Loy et al. |
| 6,045,539 A | 4/2000 | Menyhay |
| 6,116,468 A | 9/2000 | Nilson |
| 6,117,114 A | 9/2000 | Paradis |
| 6,206,861 B1 | 3/2001 | Mayer |
| 6,227,391 B1 | 5/2001 | King |
| 6,708,363 B2 | 3/2004 | Larsen |
| 6,911,025 B2 | 6/2005 | Miyahara |
| 6,994,315 B2 | 2/2006 | Ryan et al. |
| RE39,107 E | 5/2006 | Shaw |
| 7,083,605 B2 | 8/2006 | Miyahara |
| 7,184,825 B2 | 2/2007 | Leinsing et al. |
| 7,198,611 B2 | 4/2007 | Connell et al. |
| 7,282,186 B2 | 10/2007 | Lake, Jr. et al. |
| 7,452,349 B2 | 11/2008 | Miyahara |
| D607,325 S | 1/2010 | Rogers et al. |
| 7,682,561 B2 | 3/2010 | Davis et al. |
| 7,704,935 B1 | 4/2010 | Davis et al. |
| 7,755,071 B2 | 7/2010 | Polsinelli |
| 7,762,524 B2 | 7/2010 | Cawthon et al. |
| 7,780,794 B2 | 8/2010 | Rogers et al. |
| 7,794,675 B2 | 9/2010 | Lynn |
| 7,887,516 B2 | 2/2011 | Young |
| 7,922,701 B2 | 4/2011 | Buchman |
| 7,985,302 B2 | 7/2011 | Rogers et al. |
| 8,065,773 B2 | 11/2011 | Vaillancourt et al. |
| 8,113,731 B2 | 2/2012 | Cable, Jr. et al. |
| 8,167,847 B2 | 5/2012 | Anderson et al. |
| 8,172,825 B2 | 5/2012 | Solomon et al. |
| 8,177,761 B2 | 5/2012 | Howlett et al. |
| 8,206,514 B2 | 6/2012 | Rogers et al. |
| 8,231,587 B2 | 7/2012 | Solomon et al. |
| 8,231,602 B2 | 7/2012 | Anderson et al. |
| 8,328,767 B2 | 12/2012 | Solomon et al. |
| 8,343,112 B2 | 1/2013 | Solomon et al. |
| 8,419,713 B1 | 4/2013 | Solomon et al. |
| 8,523,830 B2 | 9/2013 | Solomon et al. |
| 8,523,831 B2 | 9/2013 | Solomon et al. |
| D695,398 S | 12/2013 | Solomon et al. |
| 8,628,501 B2 | 1/2014 | Hadden |
| 8,641,681 B2 | 2/2014 | Solomon et al. |
| 8,647,308 B2 | 2/2014 | Solomon et al. |
| 8,647,326 B2 | 2/2014 | Solomon et al. |
| 8,784,388 B2 | 7/2014 | Charles |
| 2003/0153865 A1 | 8/2003 | Connell et al. |
| 2003/0181849 A1 * | 9/2003 | Castellanos ........... A61M 1/285 |
| | | 604/29 |
| 2004/0004019 A1 | 1/2004 | Busch |
| 2004/0039341 A1 | 2/2004 | Ranalletta |
| 2004/0258560 A1 | 12/2004 | Lake, Jr. et al. |
| 2004/0267182 A1 * | 12/2004 | Davis ................... A61L 2/0088 |
| | | 604/2 |
| 2005/0054991 A1 * | 3/2005 | Tobyn ............... B65D 83/0011 |
| | | 604/290 |
| 2005/0124970 A1 | 6/2005 | Kunin et al. |
| 2005/0147524 A1 | 7/2005 | Bousquet |
| 2006/0030827 A1 | 2/2006 | Raulerson |
| 2007/0113861 A1 | 5/2007 | Knudsen et al. |
| 2007/0179452 A1 | 8/2007 | Kosinski |
| 2007/0202177 A1 | 8/2007 | Hoang |
| 2007/0225660 A1 | 9/2007 | Lynn |
| 2008/0027399 A1 | 1/2008 | Harding et al. |
| 2008/0147047 A1 | 6/2008 | Davis et al. |
| 2008/0177250 A1 | 7/2008 | Howlett et al. |
| 2008/0235888 A1 | 10/2008 | Vaillancourt et al. |
| 2009/0028750 A1 | 1/2009 | Ryan |
| 2009/0062766 A1 * | 3/2009 | Howlett ............... A61M 39/165 |
| | | 604/411 |
| 2009/0099529 A1 | 4/2009 | Anderson et al. |
| 2009/0149819 A1 | 6/2009 | Chelak |
| 2010/0000040 A1 | 1/2010 | Shaw et al. |
| 2010/0047123 A1 | 2/2010 | Solomon et al. |
| 2010/0049170 A1 * | 2/2010 | Solomon ............. A61M 39/162 |
| | | 604/539 |
| 2010/0242993 A1 | 9/2010 | Hoang et al. |
| 2010/0331726 A1 | 12/2010 | Steube et al. |
| 2011/0030726 A1 | 2/2011 | Vaillancourt et al. |
| 2011/0054440 A1 | 3/2011 | Lewis |
| 2011/0232020 A1 | 9/2011 | Rogers et al. |
| 2012/0022469 A1 | 1/2012 | Alpert |
| 2012/0039765 A1 | 2/2012 | Solomon et al. |
| 2012/0109073 A1 | 5/2012 | Anderson et al. |
| 2012/0296284 A1 | 11/2012 | Anderson et al. |
| 2013/0006194 A1 | 1/2013 | Anderson et al. |
| 2013/0072909 A1 | 3/2013 | Solomon et al. |
| 2013/0338644 A1 | 12/2013 | Solomon et al. |

FOREIGN PATENT DOCUMENTS

| | | |
|---|---|---|
| JP | 2007-532186 A | 11/2007 |
| JP | 2009-544451 A | 1/2008 |
| JP | 2008-253775 A | 10/2008 |
| JP | 2009-526581 A | 7/2009 |
| JP | 2010-511482 A | 4/2010 |
| WO | 2006/037434 A1 | 4/2006 |
| WO | 2008014447 A2 | 1/2008 |
| WO | WO-2008/014438 | 1/2008 |
| WO | WO-2008/070220 | 6/2008 |
| WO | 2009/002474 A1 | 12/2008 |
| WO | 2011028722 A2 | 3/2011 |
| WO | 2011/068531 A1 | 6/2011 |

OTHER PUBLICATIONS

Final Office Action in U.S. Appl. No. 14/246,723, dated Apr. 3, 2015, 15 pages.

Final Office Action in U.S. Appl. No. 14/246,723 dated Dec. 13, 2016, 22 pages.

Final Office Action in U.S. Appl. No. 14/246,723 dated Apr. 23, 2018, 13 pages.

(56) References Cited

OTHER PUBLICATIONS

Non-Final Office Action in U.S. Appl. No. 14/246,723 dated Aug. 27, 2018, 10 pages.
PCT International Search Report and Written Opinion in PCT/US2012/054787, dated Nov. 22, 2012, 11 pgs.

* cited by examiner

SYRINGE WITH DISINFECTING TIP FEATURE

CROSS-REFERENCE TO RELATED APPLICATIONS

This application is a continuation of U.S. patent application Ser. No. 13/250,097 filed Sep. 30, 2011, the disclosure of which is hereby incorporated by reference in its entirety.

TECHNICAL FIELD

The present invention relates to syringe assemblies and particularly to syringe assemblies comprising a disinfecting reservoir collar to ensure adherence to aseptic techniques for use in flush procedures for vascular access devices (VAD's).

BACKGROUND

VAD's are commonly used therapeutic devices and include intravenous (IV) catheters. There are two general classifications of VAD's, peripheral catheters and central venous catheters. To ensure VAD's are used and maintained correctly, standards of practice have been developed, which include a cleaning procedure, commonly referred to as flushing a catheter.

VAD standards of practice usually recommend that flush procedures be performed after catheter placement, before fluid infusion, and before and after drug administration, blood sampling, transfusions and parenteral nutrition. The goal of these flush procedures is to confirm catheter patency, avoid drug incompatibilities, ensure complete drug dose administration, prevent thrombus formation and minimize the risk of blood stream infections. Flush procedures require different types and amounts of flush solutions. The most commonly used flush solutions are saline and/or heparin lock solution. The type of flush solution and amount vary depending on the specific type of catheter. Flush solution volumes between 5 and 10 ml are most common but can range from 1 ml to 20 ml.

For flush procedures, an IV line refers to a system that can include a VAD, a tubing set with clamp and a VAD connector as a termination. Common types of VAD connectors are covered by pierceable septums or pre-slit septums made of rubber or another elastomeric material, which permits insertion of a sharp needle cannula in order to infuse fluids into or to withdraw fluids from the catheter. Upon withdrawal of the needle cannula, the septum seals itself. Ports having pre-slit septums are used with blunt plastic cannula or the frusto-conically shaped tip of a syringe barrel. The syringe tip or the blunt plastic cannula (which is usually attached to a syringe) is gently pushed through the pre-slit septum to establish fluid communication.

IV valves, another type of VAD connector that does not require a needle having a sharp tip, are activated by the frusto-conically shaped tip of a syringe barrel to allow fluid communication between the interior of the syringe and the catheter. These valves may contain features for delivering fluid from a storage compartment in the valve to the catheter, and are referred to in the art as positive displacement valves. Such a valve is taught in U.S. Pat. No. 6,206,861.

Bacteria and other microorganisms may gain entry into a patient's vascular system from access hubs and ports/valves upon connection to the VAD to deliver the fluid or pharmaceutical. Each access hub (or port/valve or connection) is associated with some risk of transmitting a catheter related bloodstream infection (CRBSI), which can be costly and potentially lethal.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Current "recommended practice" for aseptic IV line maintenance and IV drug delivery practices require adherence to a stepwise process referred to as "SASH." During the first step of the process, the clinician cleans/disinfects (generally with an alcohol swab) the VAD connector. Second, a syringe containing saline is used to flush the IV line or catheter (Saline flush), and then the VAD connector is disinfected a second time. Third, the fluid or pharmaceutical therapy is administered through the IV line or catheter (Administer therapy), the VAD connector is disinfected a third time, followed by a second Saline flush step. The final step, which is dependent upon the patient's need and institutional policy, is a final disinfection of the VAD connector followed by a Heparin lock step, where a small amount of heparin is injected into the IV line or catheter to prevent the formation of thrombi or blood clots. At the conclusion of this tedious stepwise process, the inlet port of the VAD connector is left exposed to the environment. This "recommended practice" requires disinfecting the VAD connector after each step, and makes IV line maintenance a very burdensome and time consuming process. Because the process is so cumbersome, clinicians very rarely implement this "recommended practice" in its entirety, and, thus, patients are exposed to the risk of contracting CRBSIs. Microorganisms populate exposed connector inlet surfaces, and, when the "recommended practice" is not adhered to, the microorganisms can enter the IV line during flushing. Furthermore, blood reflux into the IV line or catheter can cause clot formation inside the lines, and microorganisms from the connector inlet surfaces can colonize blood clots inside the lines and infect the patients during flushing.

A product currently available that aims to combat the problems associated with contaminated VAD connectors is the SwabCap®. This device disinfects a VAD connectors by covering the connector and protecting it from touch and airborne contamination after the cap has been applied. As the SwabCap® is twisted onto VAD connector, a foam pad inside the cap is compressed, releasing the isopropyl alcohol that bathes and passively disinfects the top and threads of the VAD connector while the cap is in place. Friction between the SwabCap® and VAD connector is essential to ensure proper swabbing and disinfecting as the twisting action helps focus the alcohol on the targeted areas. However, for several reasons, the SwabCap® falls short of accomplishing the desired goal of effectively cleaning and disinfecting the VAD connector. First, the caps do not always engage the threads on the catheter hub, so that friction during swabbing may be inefficient. Additionally, the caps are small, and thus, may result in touch contamination when they are being removed. Despite the fact that the caps are bright orange in color so that compliance can be visually confirmed, because the SwabCap® is a separate entity, only the most diligent clinician will utilize the cap after every step of the flush process. Thus, the cap does not ensure compliance with aseptic technique.

Substantial morbid and mortal risk is, therefore, associated with a number of routine procedures defined primarily by the uncontrollable diligence of the clinician administering the therapy. Unfortunately, the result is that a substantial degree of unnecessary risk and injury, in the form of CRBSIs, to patients occurs. There is a need, therefore, for a flush syringe assembly that promotes compliance with aseptic technique by eliminating the additional swabbing and disinfecting steps.

SUMMARY

Embodiments of the present invention are directed to a syringe assembly for use in flush applications. Syringe assemblies according to a first aspect of the present invention include a plunger rod, a syringe barrel, and a reservoir collar that permit disinfection of the hub of a VAD connector upon connection to the device. The features providing for disinfection allow the clinician to substantially achieve the effects of aseptic techniques without the need for added swabbing steps and diligence on the part of the clinician.

In one or more embodiments, the disinfection is provided by a reservoir collar that contains a disinfectant housed within a compartment in the reservoir collar.

In one variant, the reservoir collar contains an absorbent material that surrounds a tip that is adapted for connection to a VAD. The absorbent material absorbs the disinfectant, and, upon connection to the hub of a VAD connector, compresses toward the syringe barrel while disinfecting the hub. The disinfectant can be a fluid, a foam, or a gel.

In a specific embodiment, the reservoir collar surrounds a connector collar adapted for connection to the hub of a VAD connector. In another specific embodiment, the connector collar is a luer connector.

A second aspect of the present invention pertains to a method of disinfecting a VAD connector. The method according to one embodiment comprises connecting a flush syringe assembly to the hub of a VAD connector, wherein the flush syringe assembly includes a plunger rod, a syringe barrel, and a reservoir collar that permits disinfection of the hub of a VAD connector upon connection to the device. The method allows the clinician to substantially achieve the effects of aseptic techniques without the need for added swabbing steps and diligence on the part of the clinician.

In a specific embodiment, the method comprises connecting a flush syringe assembly to a hub of the vascular access device, wherein connecting includes frictionally engaging a reservoir having a collar and a tip on the flush syringe with the hub vascular access device such that the hub contacts an antimicrobial agent contained within the reservoir. As noted above, the reservoir can contain an absorbent material, and the reservoir can include a first tip and a second tip, and the flush syringe includes a seal covering the reservoir and the first and second tip. In such construction, upon connecting the flush syringe assembly to the hub, the seal is broken to expose the second tip to the antimicrobial agent. The reservoir further can comprises threads that engage threads on the hub, and connecting occurs by engaging the threads on the hub and the reservoir by twisting the vascular access device with respect to the flush syringe. Upon connection, the hub contacts the antimicrobial agent and the absorbent material.

DETAILED DESCRIPTION

Figure 1:
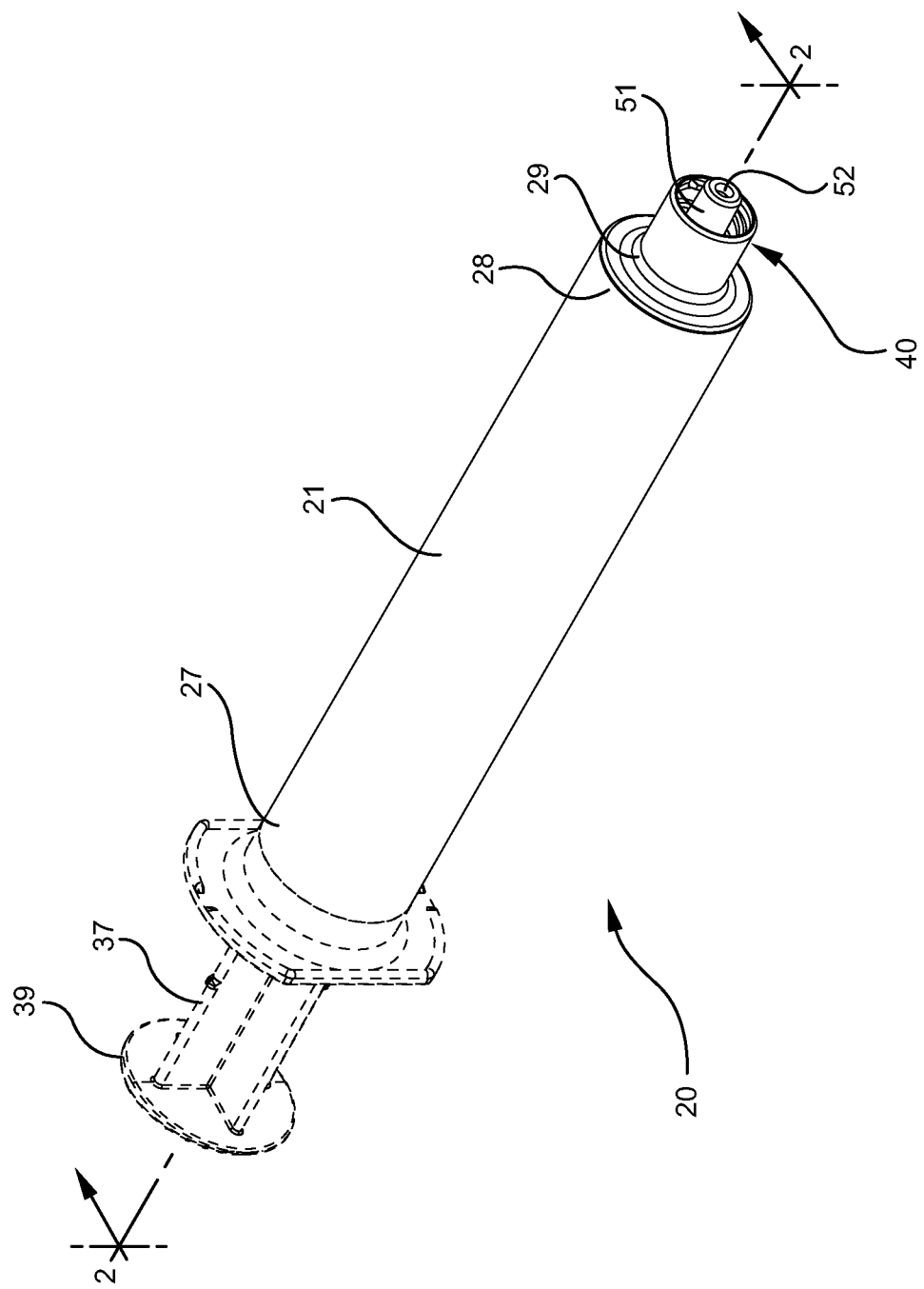
FIG. 1 is a perspective view of a flush syringe assembly according to an embodiment of the present invention.

Before describing several exemplary embodiments of the invention, it is to be understood that the invention is not limited to the details of construction or process steps set forth in the following description. The invention is capable of other embodiments and of being practiced or being carried out in various ways.

With respect to terms used in this disclosure, the following definitions are provided.

Reference to "flush syringe assembly" includes syringes that are indicated for use in the flushing of VADs. The practice of flushing ensures and maintains catheter patency and helps prevent the mixing of incompatible pharmaceuticals.

As used herein, the use of "a," "an," and "the" includes the singular and plural.

As used herein, the term "catheter related bloodstream infection" or "CRBSI" refers to any infection that results from the presence of a catheter or IV line.

As used herein, the term "microorganism" refers to a microbe or organism that is unicellular or lives in a colony of cellular organisms. Microorganisms are very diverse; they include, but are not limited to bacteria, fungi, archaea, and protozoans. Microorganisms are often the cause of CRBSIs. The most common microorganisms associated with CRBSIs include, but are not limited to, *Staphylococcus aureus* and epidermis, *Enterococcus faecalis, Escherichia coli, Pseudomonas aeruginosa,* and *Candida albicans.*

As used herein, the terms "antimicrobial agent" or "antimicrobial" refers to substances that kill or inhibit the growth of microorganisms such as bacteria, fungi, archaea, or protozoans. Antimicrobial agents either kill microbes, or prevent the growth of microbes.

As used herein, the term "disinfectant" refers to antimicrobial substances that are used on non-living objects or outside the body, e.g., on the skin.

In one or more embodiments, disinfectants or antimicrobial agent include, but are not limited to, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, dichlorobenzyl alcohol, dehydroacetic acid, hexetidine, triclosan, hydrogen peroxide, colloidal silver, and mixtures thereof.

As used herein, the term "absorbent material" refers to a material having capacity or tendency to absorb or soak up another substance. In one or more embodiments, the absorbent material has a tendency to absorb a disinfectant or antimicrobial. Absorbent materials may include sponges, absorbent cottons, other absorbent fabrics, and synthetic polymer matrices.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the VAD. A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

Figure 2:
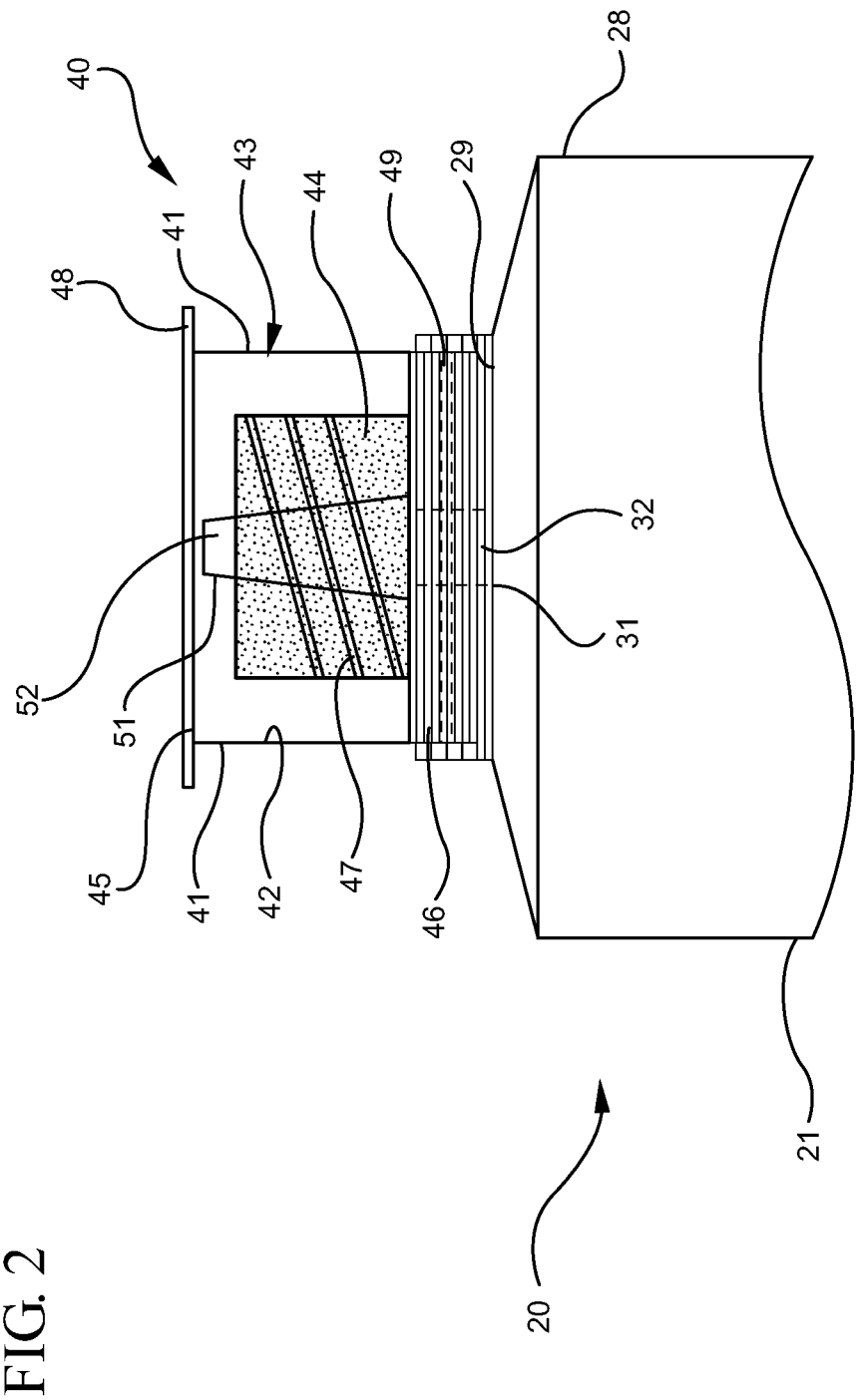
FIG. 2 is an enlarged partially cross-sectioned side elevation view of the assembled reservoir collar attached to flush syringe assembly of FIG. 1.
Figure 3:
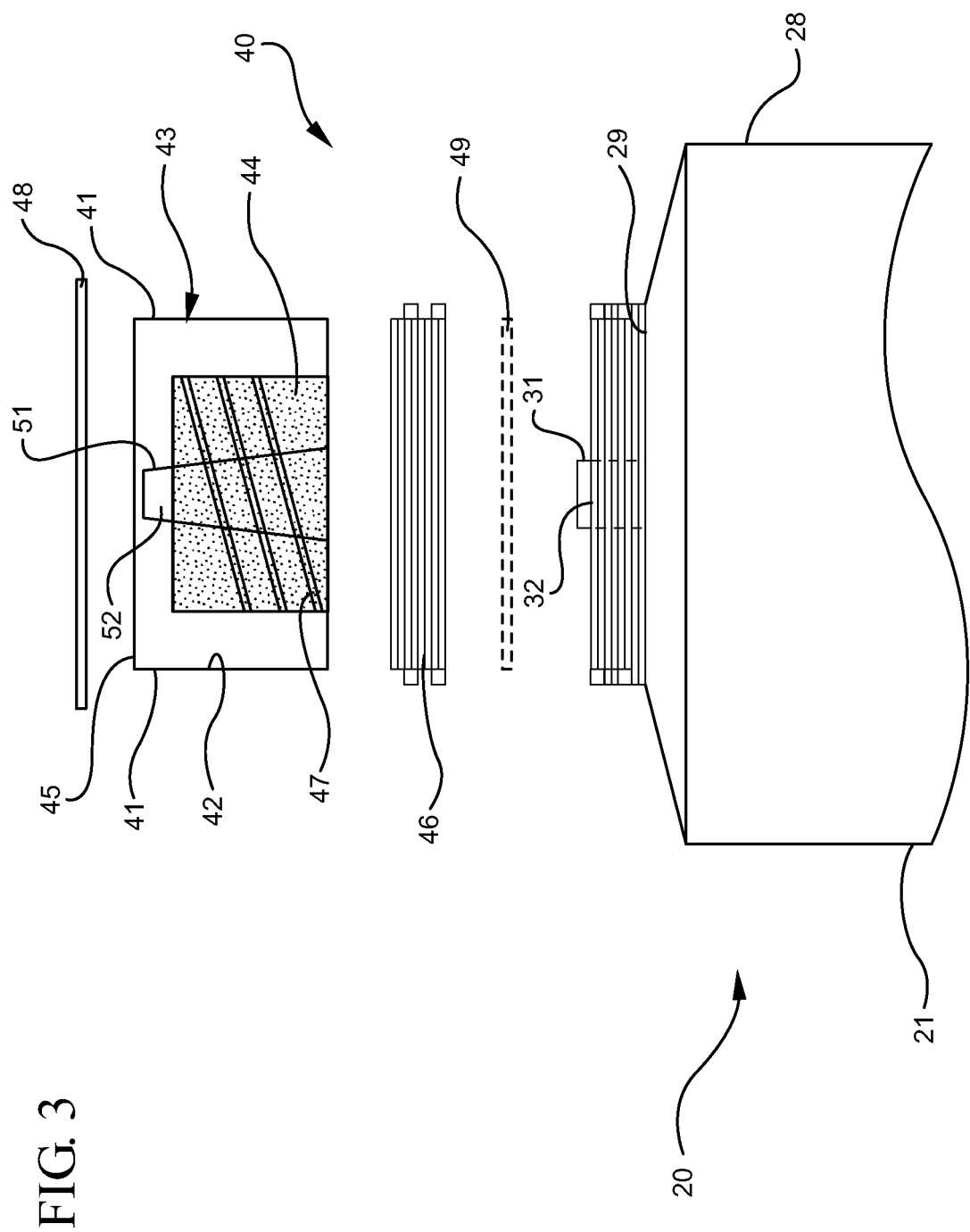
FIG. 3 is an enlarged partially cross-sectioned side elevation view of the components of the reservoir collar which attaches to the flush syringe assembly of FIG. 1.
Figure 9:
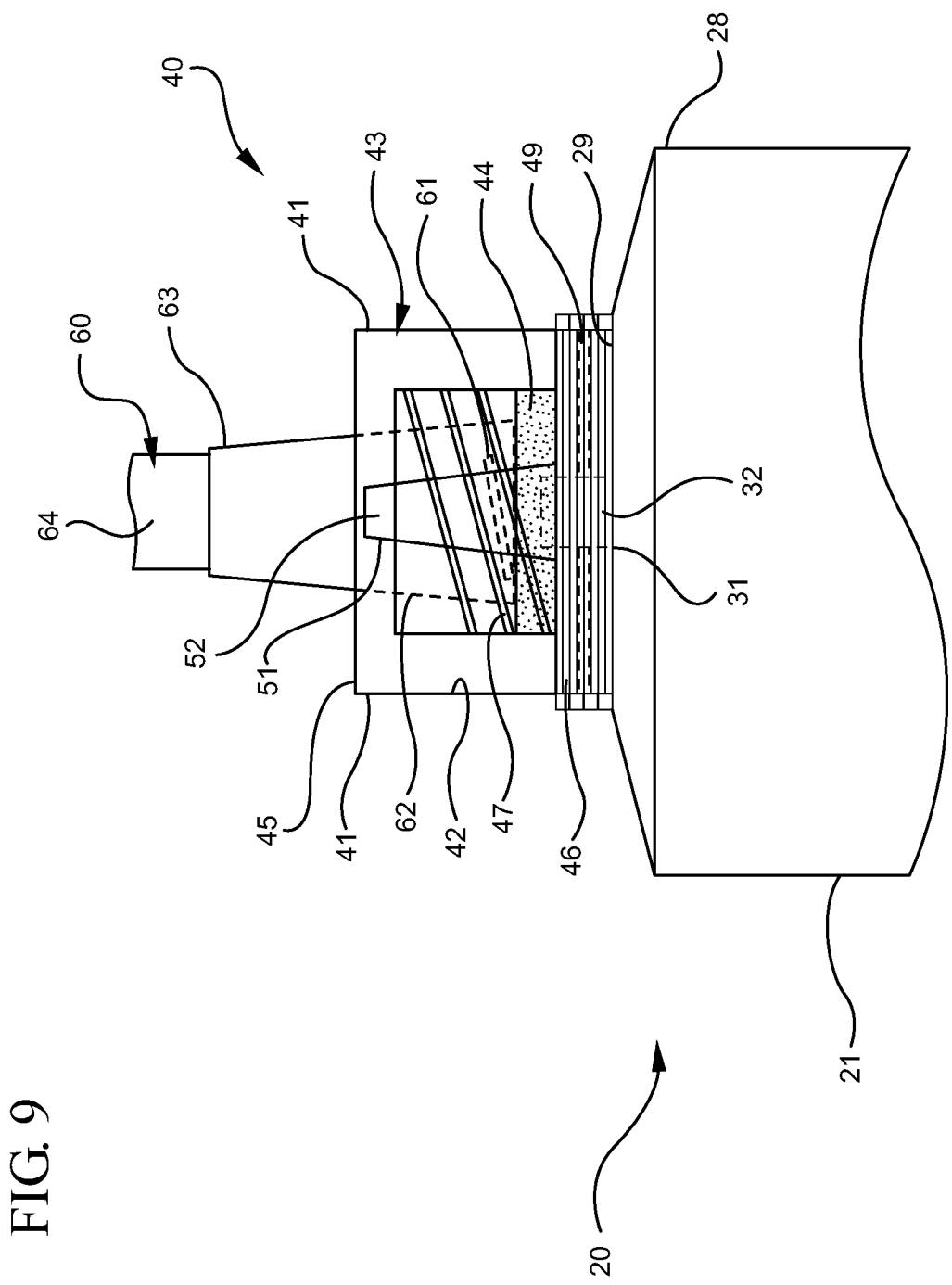
FIG. 9 is an enlarged partially cross-section side elevation view of the reservoir collar illustrating compression of the absorbent material upon connection to the hub of a VAD connector.
Figure 10:
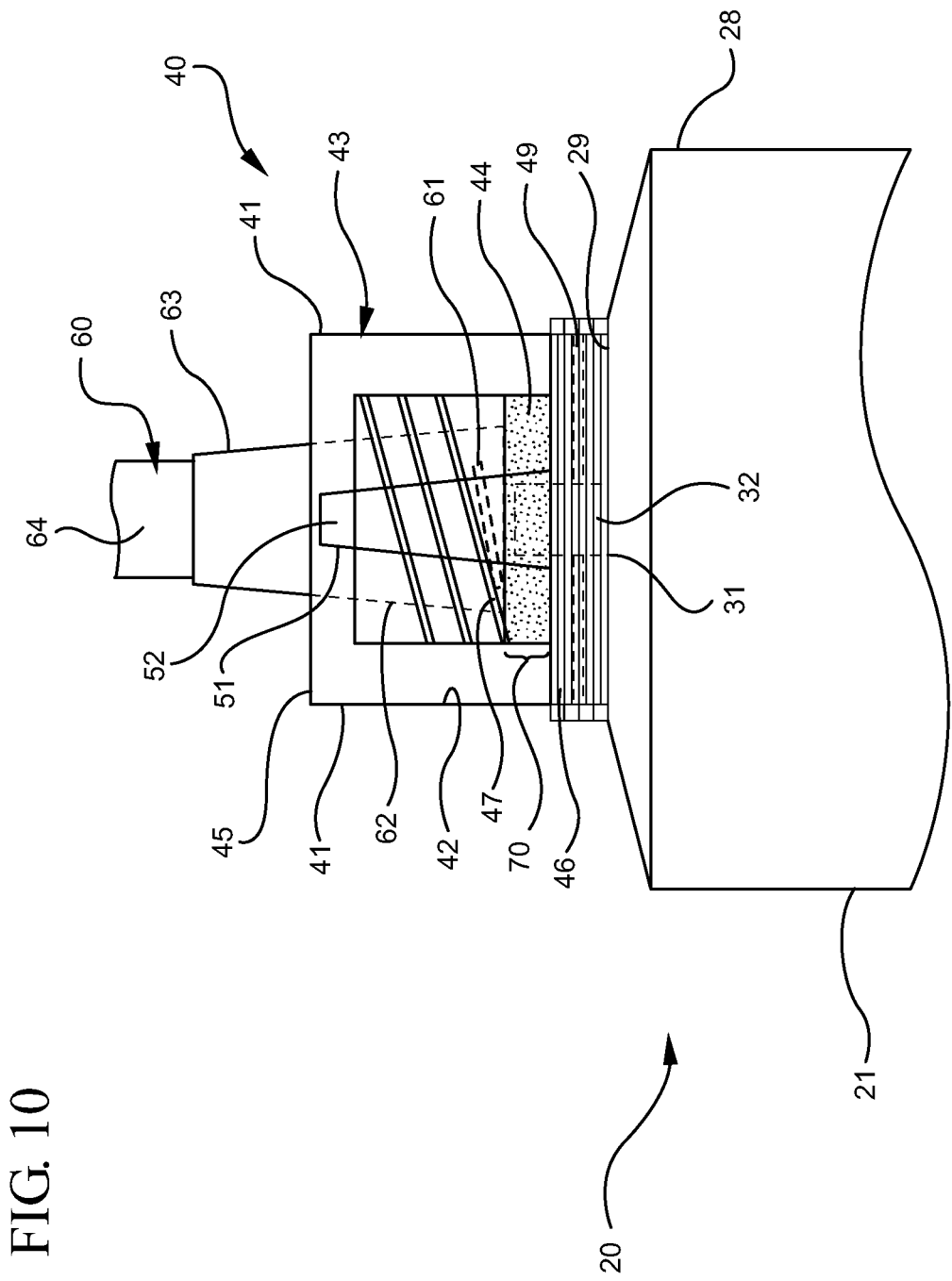
FIG. 10 is an enlarged partially cross-sectioned side elevation view of an alternative embodiment of the reservoir collar.
Figure 11:
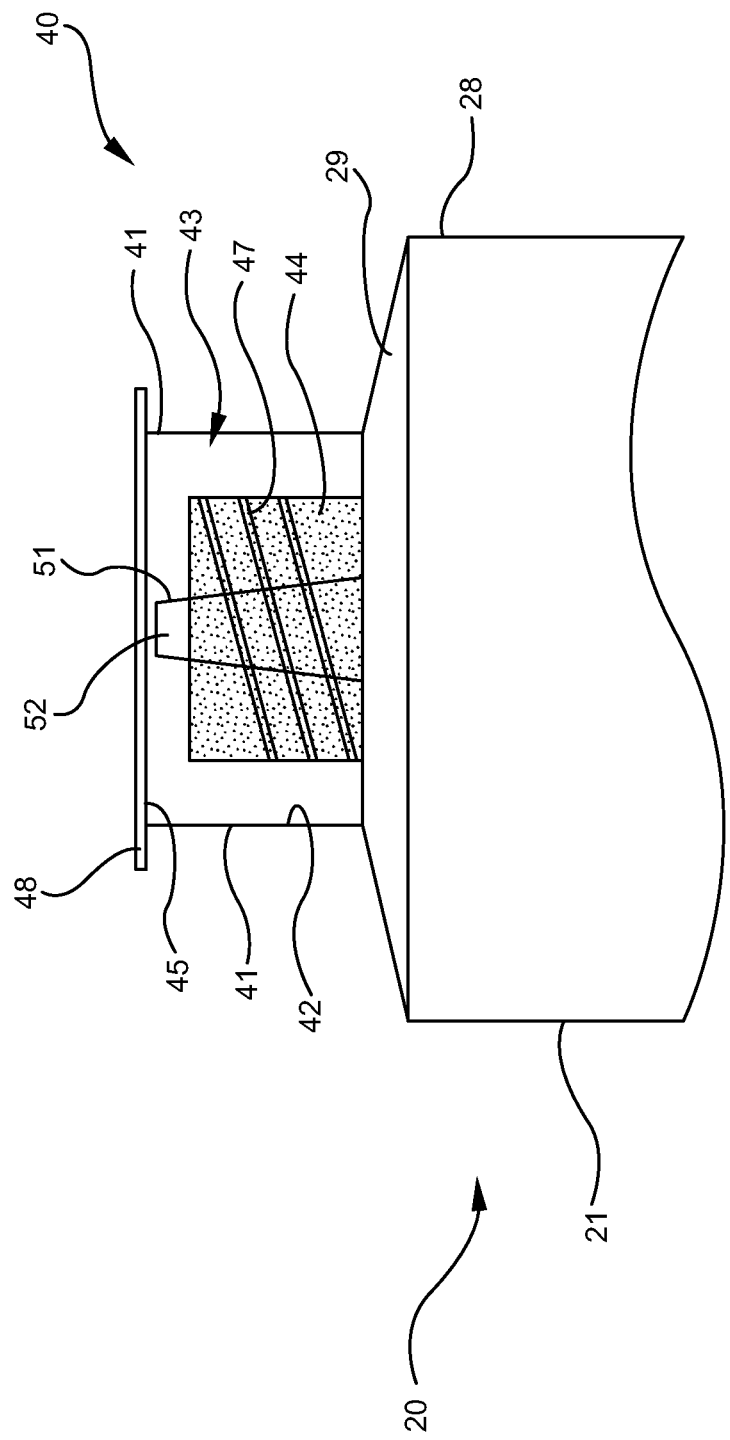
FIG. 11 is an enlarged partially cross-sectioned side elevation view of the flush syringe assembly, illustrating an alternative embodiment of the reservoir collar for connection to the syringe assembly of FIG. 1.

Provided are syringe assemblies that include a plunger rod and a syringe barrel, that incorporate an element for disinfecting the hub of a VAD. The assembled syringe assembly is shown in FIGS. 1 and 2, with the components shown separately in FIGS. 3-9. Alternative embodiments of the present invention are shown in FIGS. 10-11 Referring to FIGS. 1-3, a syringe assembly 20 according to the present invention generally comprises a barrel 21, including a side wall having an inside surface defining a chamber for retaining fluid. The barrel 21 further includes an open proximal end 27 and a distal end 28 having a distal wall 29 with an elongated first tip 31 extending distally therefrom and having a first passageway 32 therethrough in fluid communication with the chamber, the tip adapted for connection to a reservoir collar 40. The distal wall 29 may comprise a plurality of threads for attachment to the reservoir collar 40.

An plunger rod 37 includes distal portion 38 and a proximal portion 39, the plunger rod further comprising a distal end including a stopper slidably positioned in fluid-tight engagement with the inside surface of the barrel for drawing fluid into and driving fluid out of the chamber by movement of the stopper relative to the barrel, the plunger rod 37 extending outwardly from the open proximal end 27 of the barrel, the stopper having a distal surface.

Figure 5:
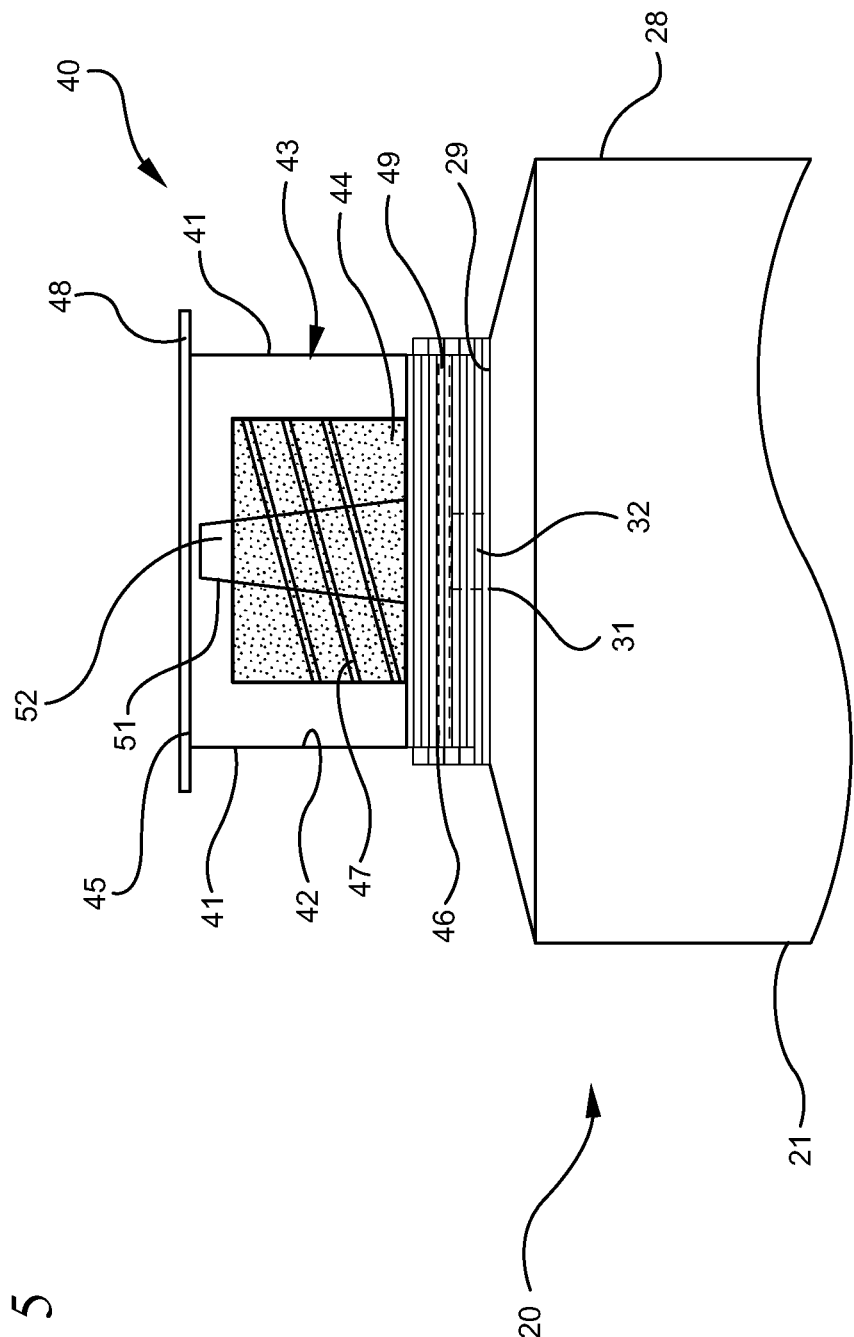
FIG. 5 is an enlarged partially cross-sectioned side elevation view of the assembled reservoir collar being attached to the flush syringe assembly of FIG. 1.
Figure 6:
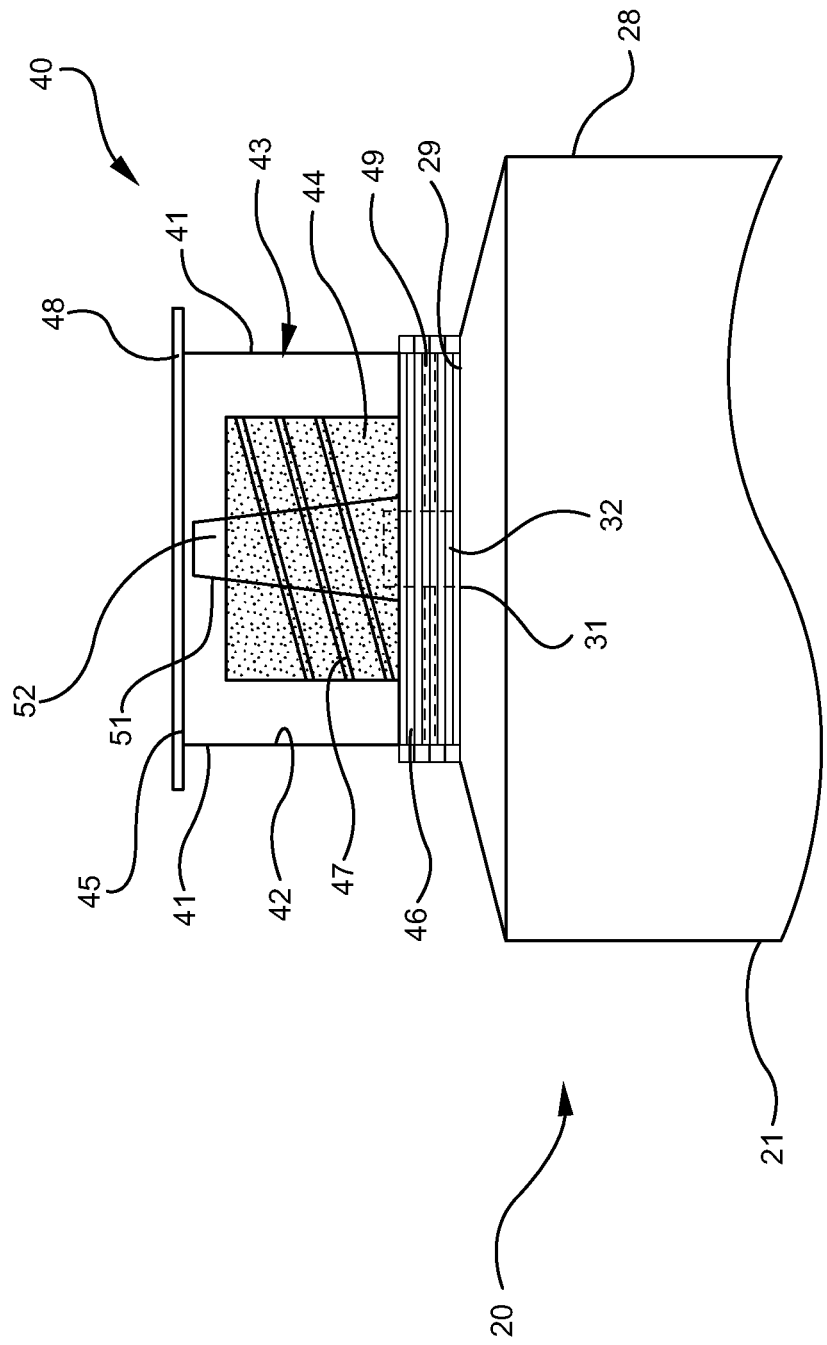
FIG. 6 is an enlarged partially cross-sectioned side elevation view of the reservoir collar attached to the flush syringe assembly of FIG. 1, illustrating how the first tip of the syringe barrel attaches interlocks with the second tip of the reservoir collar.

A reservoir collar 40 mounted on the distal end 28 of the barrel and surrounding the first tip 31, the reservoir collar 40 including at least one side wall 41 having an inside surface 42 defining a compartment 43 containing a disinfectant or antimicrobial agent, a sealed distal end 45, and a proximal end 46 adjacent the distal wall 29 of the barrel, with a second tip 51 extending distally therefrom having a second passageway 52 therethrough in fluid communication with said first passageway 32, the second tip 51 adapted for connection to a hub of a vascular access device. The reservoir collar 40 may comprise a plurality of threads 47 on the inside surface for connection to a vascular access device. The reservoir collar 40 may comprise a plurality of threads on the proximal end for attachment to the distal wall 29 of the barrel. Referring to FIG. 5, upon manufacture, the flush syringe assembly 20 can be provided with the reservoir collar 40 partially threaded at the proximal end 46 onto the distal wall 29 of the barrel. The seal 49, is not yet pierced. Referring to FIG. 6, to activate the reservoir collar 40, the clinician can twist the proximal end 46 onto the distal wall 29 such that the threads tightly interlock and the first tip 31 pierces the seal 49. The first tip 31 then becomes interlocked with the second tip 51, and the first passageway 32 and the second passageway 52 become one integral passageway for fluid communication from the barrel 21 to a VAD.

The reservoir collar 40 may comprise an absorbent material 44 surrounding the second tip 51 for soaking up the disinfectant or antimicrobial agent that is housed within the compartment 43. The disinfectant or antimicrobial agent can be a fluid or a gel selected from the group consisting of selected from the group consisting of ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, dichlorobenzyl alcohol, dehydroacetic acid, hexetidine, triclosan, hydrogen peroxide, colloidal silver, and mixtures thereof.

The sealed distal end 45 of the reservoir collar 40 may comprise a removable seal 48. The removable seal 48 can comprise an aluminum peal back top. The seal can be a plastic sealed aluminum, and can be chemically-resistant, light-blocking, non-permeable, or sterile.

The reservoir collar 40 may comprise an aluminum lining adhered to the inside surface 42 of at least one side wall 41. The aluminum lining can prevent degradation of the disinfectant or antimicrobial agent, and can also provide a mechanism for ensuring compliance with aseptic conditions.

The reservoir collar 40 may be removable from the syringe assembly 20. When removable, the reservoir collar 40 comprises a pierceable seal 49 on the proximal end 46 of the reservoir collar 40. The pierceable seal 49 can be pierced by the first tip 31 upon connection to the distal wall 29 of the barrel. The pierceable seal 49 can comprise an aluminum seal. The aluminum seal can be a plastic sealed aluminum, and can be chemically-resistant, light-blocking, non-permeable, or sterile.

In an embodiment, the reservoir collar 40 surrounds a connector collar adapted for connection to the hub of the vascular access device. The connector collar can further comprise an absorbent material 44 for soaking up the disinfectant or antimicrobial agent dispersed within the connector collar. The disinfectant or antimicrobial agent can be a fluid or a gel. In a further embodiment, the reservoir collar 40 surrounds a connector collar adapted for connection to the hub of the vascular access devices, wherein the connector collar is a Luer connector.

Figure 4:
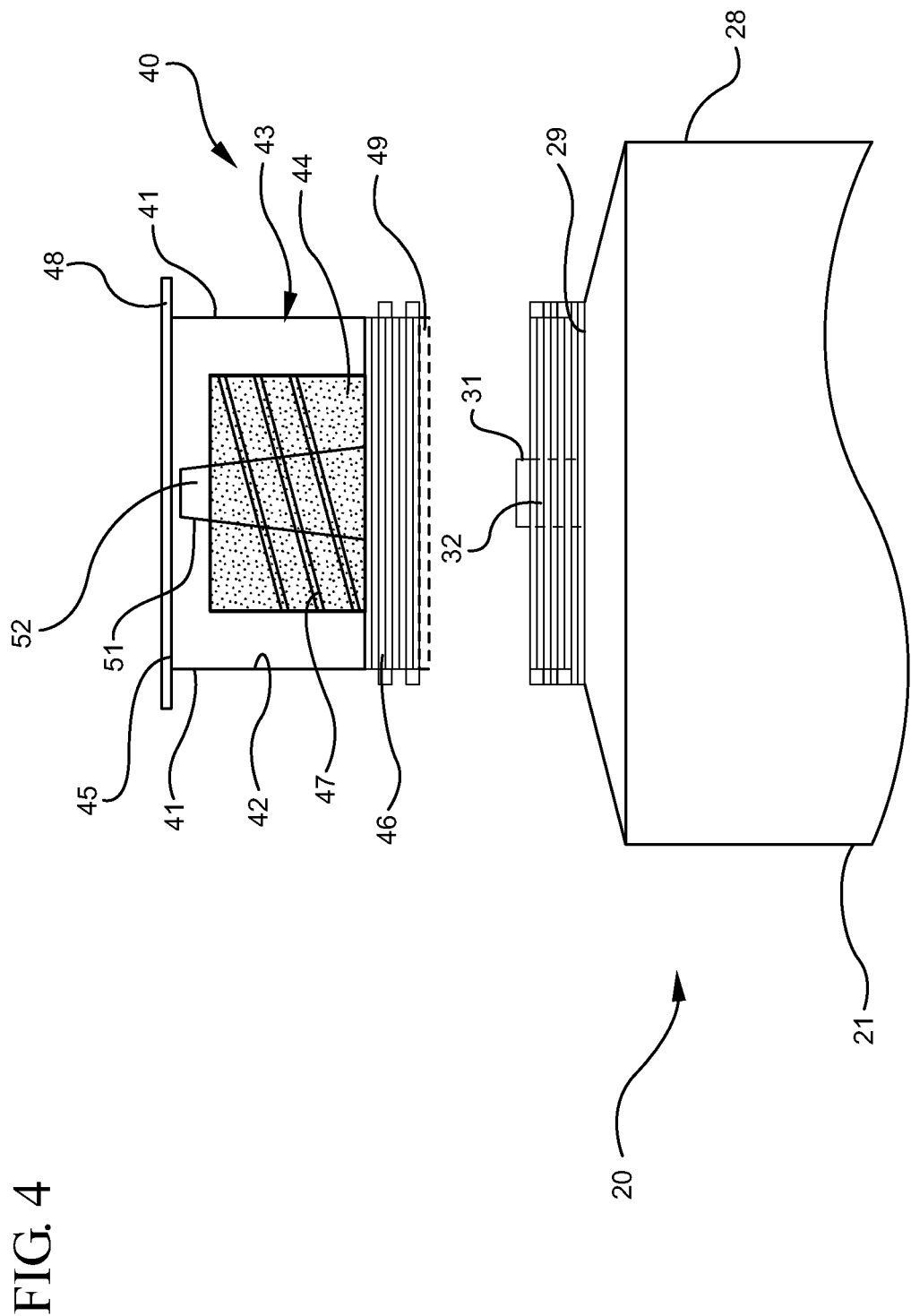
FIG. 4 is an enlarged partially cross-sectioned side elevation view of the assembled reservoir collar for attachment to flush syringe assembly of FIG. 1.

Referring to FIGS. 4-6, in operation, the assembled, removable reservoir collar 40 is attached via the proximal end 46 to the distal wall 29 of the syringe barrel 21 such that the proximal end 46 of the reservoir collar 40 is adjacent to the distal wall 29 of the syringe barrel 21. The first tip 31 interlocks with the second tip 51 such that the first passageway 32 and the second passageway 52 become one integral passageway for fluid communication to a vascular access device. Referring to FIG. 5, upon manufacture, the flush syringe assembly 20 can be provided with the reservoir collar 40 partially threaded at the proximal end 46 onto the distal wall 29 of the barrel 21. The seal 49 is not yet pierced. Referring to FIG. 6, to activate the reservoir collar 40, the clinician can twist the proximal end 46 onto the distal wall 29 such that the threads tightly interlock and the first tip 31 pierces the seal 49. The first tip 31 then becomes interlocked with the second tip 51, and the first passageway 32 and the second passageway 52 become one integral passageway for fluid communication from the barrel 21 to a VAD. Once the reservoir collar 40 has been activated by threading it onto the distal wall 29, it is now ready to be used to disinfect the hub of a VAD.

The syringe assembly 20 is filled with flush solution using known methods. Additionally, the syringe assembly 20 may be provided pre-filled from the manufacturer or supplier. The flush solution may be any solution intended for flushing or maintaining performance of VAD's. It is preferred that the flush solution be selected from the group consisting of saline flush solution and heparin lock flush solution. These solutions are known in the art and are readily available. An example of a saline flush solution includes, but is not limited to, 0.9% sodium chloride USP for injection. An example of a heparin lock flush solution includes but is not limited to 0.9% sodium chloride with 100 USP units of heparin sodium per mL or 10 USP units of heparin sodium per mL. When the first tip 31 interlocks with the second tip 51, the flush solution is communicated from the barrel 21 through the now integral first passageway 32 and second passageway 52 to a vascular access device.

Figure 8:
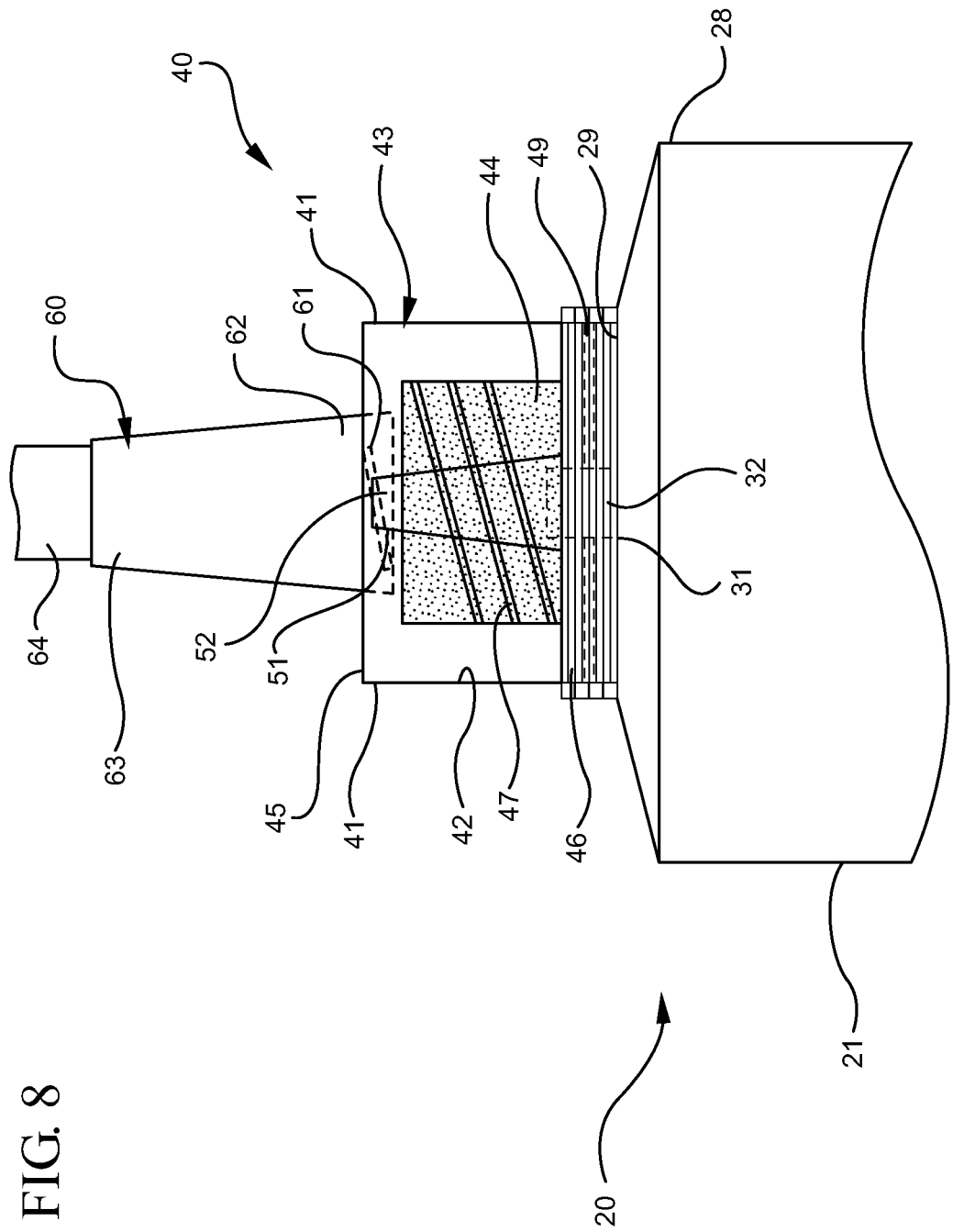
FIG. 8 is an enlarged partially cross-sectioned side elevation view of the reservoir collar illustrating attachment of the reservoir collar to the hub of a VAD connector.

The syringe assembly 20 is now ready for use in flushing a vascular access device such as a catheter or IV set. IV sets can be very complex and may include multiple injection ports, valves, and/or other components. For the purpose of illustrating the present invention, a simplified IV set or catheter hub 60 is illustrated in FIGS. 8 and 9. The hub 60 includes a housing hollow interior and a septum 61 at its proximal end 62. A hollow IV line or catheter 64 extends from the distal end 63 from the housing. The IV site may be a valve having structure for accepting the second tip 51 and being activated by the insertion of the second tip 51 to establish fluid communication with the IV line or catheter 64.

There are two general classifications of VAD's, peripheral catheters and central venous catheters. Peripheral catheters are used to access veins in the peripheral extremities such as the hand and arm. Peripheral catheters are relatively short in length ranging from about 14 mm to 48 mm in length, and are available in gauge sizes from about 16 to 24. It is believed that the most commonly used peripheral catheters are 20 gauge having an ID of about 0.81 mm (0.032 inch) and 22 gauge having an ID of about 0.66 mm (0.026 inch), and having a length of about 25 mm to 32 mm. As used herein, the term "peripheral catheter" is intended to refer to a 20 or 22 gauge catheter having a length of about 25 mm. Central venous catheters are substantially longer than peripheral catheters and are inserted in the patient and terminate near the heart.

Figure 7:
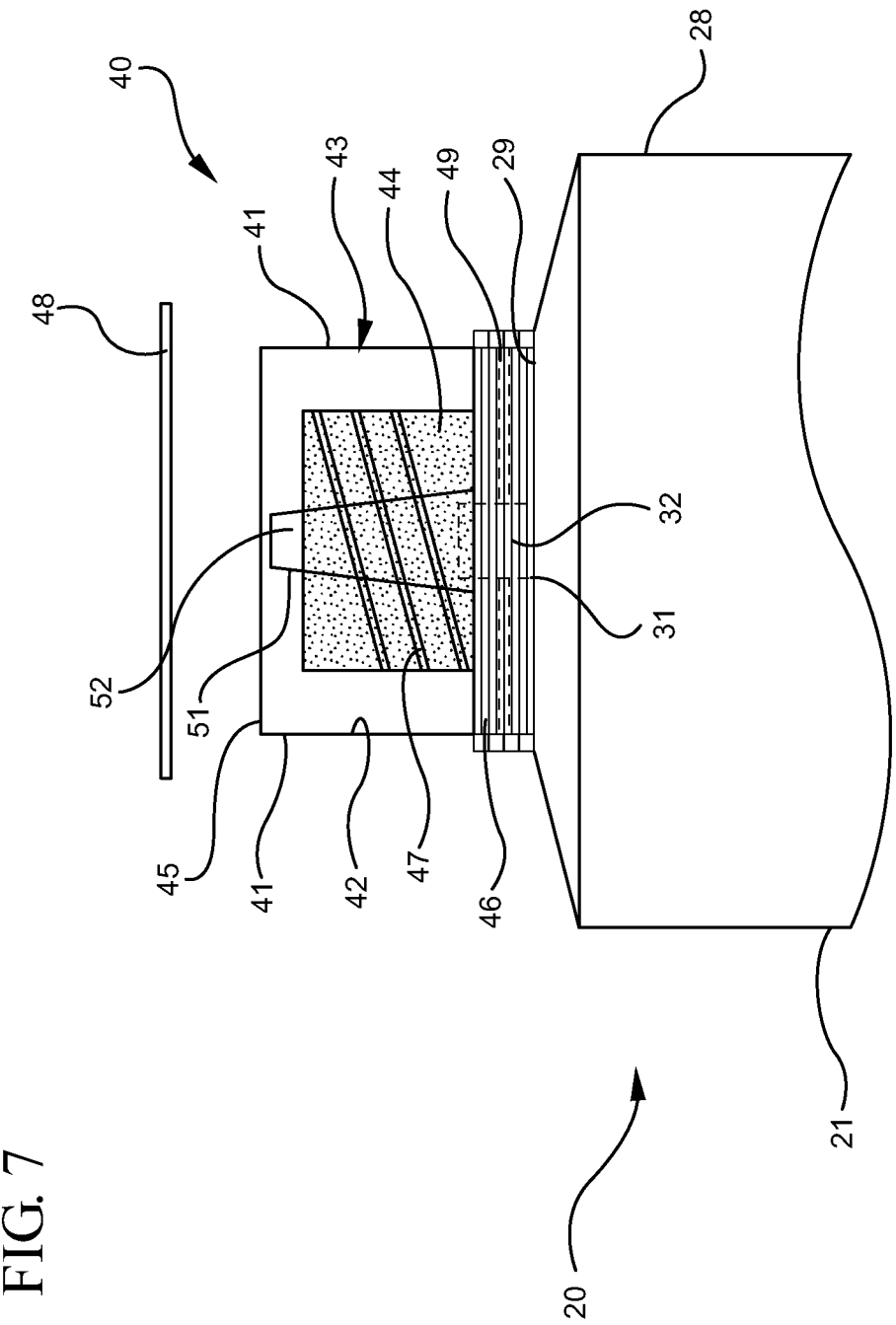
FIG. 7 is an enlarged partially cross-sectioned side elevation view of the reservoir collar illustrating removal of the seal over the end of the reservoir collar for attachment to a VAD.

Referring to FIGS. 7-9, the syringe assembly 20 when connected with reservoir collar 40 has a second tip 51 that is rendered antimicrobial because it is surrounded by an absorbent material 44 that soaks up disinfectant or antimicrobial agent contained within compartment 43. The now antimicrobial tip 51 can be connected to a vascular access device. The seal 48 is removed from the distal end 45 of the reservoir collar 40, exposing the second tip 51. As the syringe assembly 20 is connected to the hub of a vascular access device 60, the absorbent material 44 compresses creating friction. The disinfecting properties of the disinfectant or antimicrobial agent contained within the chamber 43 that has been absorbed by absorbent material 44, disinfect the hub 60, thus ensuring compliance with aseptic technique. The friction created by the compression of the absorbent material 44 is necessary to provide disinfection of the hub 60. Once the connection of the syringe assembly 20 to the hub 60 is completed, the hub is properly disinfected, and fluid communication from the barrel 21 of the syringe to the vascular access device can occur. Fluid is drawn from the barrel 21 through the integral first passageway 32 and second passageway 52 through the hub 60 and into the IV or catheter 64. Because of the presence of the reservoir collar 40, fluid communication through a vascular access device and into a patient is conducted under aseptic conditions without any additional swabbing steps and diligence on the part of the clinician.

FIG. 10 illustrates an alternative embodiment of the reservoir collar 40. Additional space 70 between the plurality of threads 47 and the proximal end 46, allows the clinician to fully rotate the syringe assembly 20 and completely disinfect the hub 60 of a vascular access device upon connection of the syringe assembly 20 to the hub 60.

FIG. 11 illustrates another embodiment of the syringe assembly 20. The reservoir collar 40 can be integrally formed on the distal wall 29 of the syringe barrel 21 with a second tip 51 with a second passageway 52 extending therethrough for fluid communication to the vascular access device. A seal 48 will contain the disinfectant or antimicrobial agent within the chamber 43 until the seal 48 is removed and the syringe assembly 20 is connected to a vascular access device. The absorbent material 44 will soak up the disinfectant or antimicrobial agent and will disinfect the hub of a vascular access device upon connection. This alternative syringe assembly is simpler to manufacture compared to the assembly of FIGS. 1-3. However, extractables may increase.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as disclosed.

What is claimed is:

1. A removable reservoir collar for connecting a syringe barrel to a vascular access device comprising:
    at least one side wall having an inside surface defining a compartment containing a compressible, friction-creating absorbent material including an absorbed disinfectant or an absorbed antimicrobial agent, and a second tip in the compartment and surrounded by the friction-creating absorbent material, the second tip extending distally from a proximal end of the reservoir collar and the second tip adapted for connection to a hub of the vascular access device and for interlocking with a first tip of the syringe barrel having a first passageway therethrough;
    a sealed distal end having a removable seal;
    a first plurality of threads on the inside surface of the reservoir collar for connection to the hub of the vascular access device;

a second plurality of threads on the proximal end of the reservoir collar adapted for connection to the syringe barrel; and a pierceable seal on the proximal end of the reservoir collar;

wherein the second tip has a passageway therethrough which, upon interlocking of the second tip with the first tip of the syringe barrel and connection of the second tip to the hub of the vascular access device, produces one integral passageway for fluid communication from the syringe barrel to the vascular access device.

2. The reservoir collar of claim 1, wherein the proximal end of the reservoir collar is threaded onto a distal wall of the syringe barrel.

3. The reservoir collar of claim 1, wherein the disinfectant or the antimicrobial agent is a fluid or a gel.

4. The reservoir collar of claim 1, further comprising a connection collar adapted for connection to the hub of the vascular access device, wherein the reservoir collar surrounds the connection collar.

5. The reservoir collar of claim 4, wherein the connection collar is a Luer connector.

6. The reservoir collar of claim 1, wherein the disinfectant or the antimicrobial agent is selected from the group consisting of ethanol, 2-propanol, butanol, methylparaben, ethylparaben, propylparaben, propyl gallate, butylated hydroxyanisole (BHA), butylated hydroxytoluene, t-butylhydroquinone, chloroxylenol, chlorohexidine, dichlorobenzyl alcohol, dehydroacetic acid, hexetidine, triclosan, hydrogen peroxide, colloidal silver, and mixtures thereof.

7. The reservoir collar of claim 1, wherein the removable seal of the distal end comprises an aluminum or a multi-layer polymer film peel back top.

8. The reservoir collar of claim 1, further comprising an aluminum lining adhered to the inside surface of the at least one side wall of the reservoir collar.

9. The reservoir collar of claim 1, wherein the absorbent material compresses toward the proximal end of the reservoir collar upon connection to the hub of the vascular access device.

10. The reservoir collar of claim 9, wherein compression of the absorbent material disinfects the vascular access device.

11. The reservoir collar of claim 1, wherein the pierceable seal on the proximal end of the reservoir collar is pierced by the first tip of the syringe barrel upon connection of the reservoir collar to the syringe barrel.

12. The reservoir collar of claim 1, wherein the pierceable seal on the proximal end of the reservoir collar is a pierceable aluminum.

13. A method of disinfecting a vascular access device, the method comprising:

removing the removable seal from the distal end of the reservoir collar of claim 1;

connecting the reservoir collar to the hub of the vascular access device, wherein connecting includes frictionally engaging the reservoir collar with the hub of the vascular access device to compress and create friction with the absorbent material contained in the compartment such that the hub contacts the disinfectant or the antimicrobial agent of the absorbent material.

14. The method of claim 13, wherein connecting further comprises engaging the first plurality of threads on the inside surface of the reservoir collar with the hub of the vascular access device by twisting the vascular access device with respect to the reservoir collar.

* * * * *